US008586377B2

(12) United States Patent
Fuerst et al.

(10) Patent No.: US 8,586,377 B2
(45) Date of Patent: Nov. 19, 2013

(54) ANALYTICAL TEST ELEMENT AND PROCESS FOR ITS PRODUCTION

(75) Inventors: Otto Fuerst, Viernheim (DE); Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/588,494

(22) Filed: Aug. 17, 2012

(65) Prior Publication Data

US 2012/0315432 A1 Dec. 13, 2012

Related U.S. Application Data

(60) Division of application No. 13/005,832, filed on Jan. 13, 2011, now Pat. No. 8,263,020, which is a continuation of application No. PCT/EP2009/058893, filed on Jul. 13, 2009.

(30) Foreign Application Priority Data

Jul. 14, 2008 (EP) ..................... 08160317

(51) Int. Cl.
*G01N 33/48* (2006.01)
(52) U.S. Cl.
USPC ........... 436/166; 422/425; 422/400; 422/427; 422/429; 422/500
(58) Field of Classification Search
USPC .......... 436/166; 422/400, 425, 427, 429, 500, 422/513
See application file for complete search history.

(56) References Cited

U.S. PATENT DOCUMENTS

| | | | | | |
|---|---|---|---|---|---|
| 2,779,662 | A | * | 1/1957 | Frey | 423/613 |
| 2,823,982 | A | * | 2/1958 | Saladin et al. | 423/337 |
| 3,107,150 | A | * | 10/1963 | Angerman | 423/610 |
| 4,292,272 | A | | 9/1981 | Kitajima et al. | |
| 4,732,849 | A | | 3/1988 | Seshimoto et al. | |
| 4,783,315 | A | | 11/1988 | Arai et al. | |
| 5,846,837 | A | | 12/1998 | Thym et al. | |
| 5,916,156 | A | | 6/1999 | Hildenbrand et al. | |
| 6,881,378 | B1 | | 4/2005 | Zimmer et al. | |
| 7,008,799 | B1 | | 3/2006 | Zimmer et al. | |
| 7,025,836 | B1 | | 4/2006 | Zimmer et al. | |
| 7,820,451 | B2 | | 10/2010 | Brauner | |
| 2005/0084982 | A1 | | 4/2005 | Brauner | |
| 2006/0002816 | A1 | | 1/2006 | Zimmer et al. | |
| 2008/0014658 | A1 | | 1/2008 | Neubert et al. | |

FOREIGN PATENT DOCUMENTS

| | | |
|---|---|---|
| DE | 19753847 | 5/1999 |
| DE | 19753848 | 6/1999 |
| DE | 102006032667 | 1/2008 |
| EP | 0821233 | 9/2002 |
| EP | 1037717 | 3/2003 |
| EP | 1039298 | 8/2004 |
| EP | 1522343 | 4/2005 |
| EP | 1593434 | 7/2008 |
| WO | WO 2004/067444 | 8/2004 |
| WO | 2005/080978 A1 | 9/2005 |

* cited by examiner

*Primary Examiner* — Lyle Alexander
(74) *Attorney, Agent, or Firm* — Roche Diagnostics Operations, Inc.

(57) ABSTRACT

An analytical test element is provided having a surface comprising a chemical detection layer on which a spreading net is disposed, the spreading net being configured to provide for the planar distribution of a liquid sample on the detection layer. The spreading net generally comprises a filament structure coated with a metallic layer that is oxidized at least on one or more surface portions thereof facing the detection layer.

15 Claims, 1 Drawing Sheet

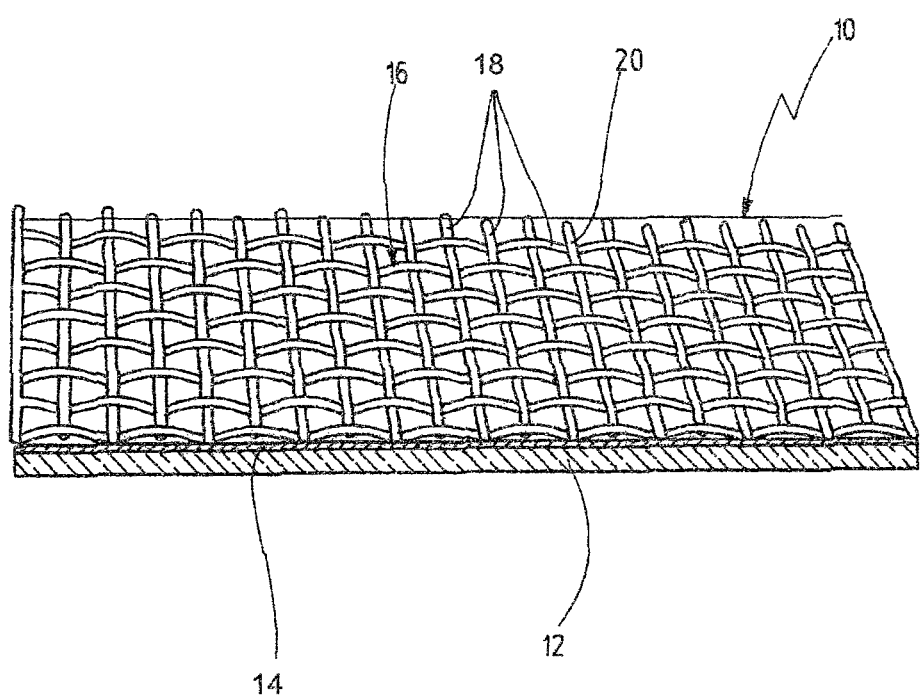

ANALYTICAL TEST ELEMENT AND PROCESS FOR ITS PRODUCTION

CLAIM OF PRIORITY

The present application is a divisional of U.S. patent application Ser. No. 13/005,832 filed on Jan. 13, 2011, now U.S. Pat. No. 8,263,020 which is a continuation application based on and claiming priority to International Application PCT/EP2009/058893, filed Jul. 13, 2009, which claims the priority benefit of European Patent Application No. 08160317.7, filed Jul. 14, 2008, each of which is hereby incorporated by reference in its entirety.

TECHNICAL FIELD OF THE INVENTION

The present application relates to analytical test elements with hydrophilicly modified surfaces, and more particularly to a process for the production of such test elements.

BACKGROUND

Analytical test elements are used in particular for the rapid qualitative and quantitative analytical determination of components of liquid samples, for example in the form of separate test strips or tape-like test material. For example, see test elements as disclosed in EP 1 039 298 B1 and EP 1 593 434 A2, the disclosures of which are each hereby incorporated herein by reference in their respective entireties. Analytical test elements can also be provided in integrated systems in which the test element is connected to a sampling device. The surface of the test element as a detection layer is typically prepared with suitable dry chemicals for the desired analysis. Important fields of use include for example medical diagnostics and environmental analysis.

Conventional test elements are usually manufactured from plastic in order to simplify their production and reduce production costs and for reasons of component stability. They therefore have a comparatively hydrophobic surface.

Methods for producing a surface coating and the uses of such surface coatings to increase the surface tension of objects are generally known. These objects can for example be an analytical test element on which sample liquid is transported from a sample application site to a determination site, where a detection site is downstream of the sample application site in the direction of transport. The surface coating is obtained by depositing a coat of at least one element that can be oxidized by water or an alloy that can be oxidized by water and subsequent action of boiling water or water vapor on the deposited layer. All those objects come into consideration as objects to be coated whose surface has a lower hydrophilicity in the uncoated state than in the coated, after-treated state such as plastic, metal, glass, ceramic, paper, fleece, cardboard etc. where the objects can be of any design e.g. planar, three-dimensional, porous etc. See, for example, DE 197 53 848 A1, the disclosure of which is hereby incorporated herein by reference in its entirety.

Hydrophilic surfaces can thus be generated in order that a sample spreads thereon as a result of wetting and therefore moves in a certain direction between two such surfaces driven by capillary forces. Both surfaces are topologically comparable, they are also functionally the same and do not touch. They typically serve to transport liquid from a sample application site to a determination site.

Because the aqueous sample should wet the surface well, the surface is provided with a spreading agent for this purpose, for example in the form of spreading nets coated with a wetting agent.

The use of spreading nets especially for test strips is known. They are usually fabrics, knitted fabrics, etc. made of plastic fibers which are provided with a surfactant coating for hydrophilization. Anionic or neutral surfactants such as for example DONS (docusate sodium) are usually used for this purpose. However, the quality of these coatings is subject to variations and becomes more difficult to realize the finer the material structure is. In particular zones of accumulation and depletion occur in a net due to capillary drying effects of a dissolved surfactant. In addition a number of surfactants have a tendency to creep.

Alternative methods have been proposed in which plastic surfaces are hydrophilized by planar coating with a metallic material and subsequent oxidation of the material with water. See, for example, EP 1 037 717 B1, the disclosure of which is hereby incorporated herein by reference in its entirety.

The object of the present invention is to provide generic test elements or filament structures with hydrophilicly modified surfaces which can be produced with the least possible effort and in a reproducible quality.

SUMMARY

This object and others that will be appreciated by a person of ordinary skill in the art have been achieved according to the embodiments of the present invention disclosed herein, including those embodiments set forth in the claims.

The term "spreading net" is understood within the scope of the present invention as a generic term for all filament structures that are suitable for spreading or distribution or transfer purposes. These include among others fabrics, interlaced yarns, knitted fabrics and fleeces. The term "filament" encompasses monofilaments as well as polyfilaments of a uniform or non-uniform material basis and dimensions. It should be mentioned that sample is typically transferable through a filament structure.

Within the scope of the present invention "analytical test element" is understood as all carrier-bound tests for medical and non-medical purposes. These carrier-bound tests have detection reagents embedded in appropriate layers of a carrier which is brought into contact with a liquid sample. The reaction of liquid sample and reagents leads to a detectable signal when a target analyte is present such as a measurable electrical signal or a color change which can be analyzed visually or with the aid of an instrument, for example by means of reflection photometry or fluorescence photometry.

Embodiments of a spreading net as described herein lay generally on a chemical detection layer of a test element. Thus, the applied sample liquid is conveyed by capillary action from the spreading net to the chemical detection layer and is also spread or dispersed on the detection layer by capillary forces at the contact sites of the spreading net and detection layer. Hence, the spreading net serves as an aid for the undirected (isotropic) planar dispersion of a liquid sample at the target site on a geometrically/topologically and functionally different surface, namely a chemical detection layer. In this process the desired intermediate retention and two-dimensional spreading of the sample occurs in the interplay with the spreading net by means of the fact that the spreading net delimits a large number of varying capillary-active interspaces and capillary gaps with respect to the detection layer which in their entirety are substantially undirected due to the surface contour of the filaments and their spatial arrangement.

The separate hydrophilized spreading nets for the test elements are simple to produce and can be introduced without difficulty into all existing test systems (for example test strips, integrated test systems). In particular they can be glued onto a test element without problems even individually without interfering with the hydrophilizing coating. The hydrophilization can be obtained in a reproducible quality and can be simply controlled. Surfactants are not typically needed in the process. Test elements can be produced with very finely structured hydrophilic spreading nets.

Embodiments of the spreading nets can be manufactured from metallic or plastic filaments or combinations thereof. Plastic filaments or finished spreading nets made therefrom are provided in a known manner with a coating of metallic material applied thereto by, for example, sputtering, metal evaporation, galvanic coating or deposition from dissolved metal compounds. The metallic material may comprise any metal-containing material, including pure metals, alloys and metal-containing mixtures. Furthermore, it is possible to apply one or more coats of the metallic material. The known, commercially available spreading nets made of plastic that are treated according to this disclosure are typically suitable for the spreading nets provided according to the embodiments disclosed herein.

The oxidation of the metallic material coating can be carried out in particular with water, alkaline or alkaline-earth hydroxides, oxygen, hydrogen peroxide, ozone, heat in the presence of atmospheric oxygen or sulfur compounds. The metallic material is oxidized at least at the surface thereof (for example by the boehmite method using hot water or water vapor). The metallic material can also be directly oxidized by sulfur-containing compounds. Furthermore, the generated oxygen-containing metal compounds can be after-treated with sulfur-containing compounds and be completely or partially converted into sulfur-containing metal compounds.

The finished oxidized coating (referred to in the following simply as "MeO layer" or "MeS layer") of the layer of metallic material is formed as a defined layer from the homogeneous metal-containing layer. No formation of zones of accumulation and depletion are observed during the generation of the MeO or MeS layer. Depletion zones can only form where to begin with no metal is present or they can form at the contact points of the filaments. The finished MeO layer or MeS layer has oxygen, hydroxyl groups or wholly or partially sulfur instead of oxygen and/or very thin layers of adsorbed water in a chemical bond on its surface which results in the hydrophilicity. The finished MeO layer or MeS layer adheres firmly to the filaments. Differences in the coating density and migration of the hydrophilic layer, which can occur with conventional surfactant coatings for example due to drying or creeping effects, are not observed. As a result the wetting behavior is reproducibly stable with respect to the applied sample even in the case of very finely structured, filigrane spreading nets.

A conventional spreading net, i.e. one which is hydrophilized with wetting agents, usually has a lower bonding strength with respect to adhesives due to the wetting agent so that in some cases a compromise has to be found between the wetting agent requirements and adhesive stability.

However, the MeO-coated spreading net can be fastened even more durably with adhesive than is the case for a conventional spreading net because the MeO layer acts as a bonding agent for the adhesive whether it be a pure MeO layer or an MeO surface that has been subsequently modified with an additional agent (e.g. a wetting agent).

In this process the adhesive may, as is often the case, be on another layer e.g. on a double-sided adhesive tape (e.g. acrylate adhesive or caoutchouc adhesive) when it comes into contact with the spreading net that has to be glued.

The adhesive can, however, also become a component of the spreading net itself by being previously introduced at a defined position in the spreading net. A spreading net that has been pre-fabricated in this manner can contain adhesive which for example is applied in a dissolved form in an organic solvent and then dried.

Thus, for example solutions of hot-melt adhesive (polyvinyl acetate, polyvinyl ester dissolved for example in methyl ethyl ketone, toluene) can be applied which during the processing of the net leads to a firm and at the same time flat adhesive bond (without an additional increase in the height of the assembly due to an adhesive tape).

The adhesive solution can be applied by known methods. For example a very precise metering by means of an ink-jet adapted method is also conceivable. In this process the adhesive can be marked in a suitable manner (e.g. by staining) so that an automated exact positioning is achieved in the subsequent processing.

For the sake of completeness it should be mentioned that fixation can also be carried out by means of the melting adhesion of the spreading net itself even if it is only at certain points or as an additional measure.

Thus, an MeO-coated spreading net can be coated with various hot-melt adhesives dissolved in solvents, dried and subsequently thermally glued. An MeO-coated spreading net can also be welded with a PET foil.

In a further experiment a strip of a conventional adhesive tape was bonded at a defined pressure in one alignment (linear) with a long strip of a somewhat wider MeO-coated spreading net and with a similar strip of a conventionally hydrophilized spreading net of the same dimensions.

This is carried out such that the overlong free pieces of the two spreading nets which approach from left and right abut centrally on the adhesive tape. These free pieces were then each folded by 180° such that over their glued material they then form on both sides the free ends of the central adhesion.

If the two free ends of the total bonded joint are now tension-loaded, the MeO-coated spreading net remained more firmly bonded to the adhesive tape than the spreading net that was conventionally coated.

If only the surface of the metallic layer is converted into MeO/MeS and the underlying metallic material is retained (whether as a metal layer below the MeO or MeS layer or as metallic filaments), its conductivity and the possibility of electrostatic charging or discharging is maintained. These properties can be utilized for the spreading net provided according to the invention for example for further processing or as fastening aid to secure it on the test element, for selective electrostatic deposition on the spreading net, in order to facilitate or accelerate the transfer or transport of the sample onto the spreading net.

However, an electrostatic charge can also be specifically avoided or conducted away. The spreading nets are typically more antistatic than those of the prior art. They can even be electrostatically controlled in a targeted manner which improves liquid transfer and/or the transition to the test element. It also reduces or even avoids contamination by (production-related) abrasion or extraneous dust.

The water uptake of a layer depends on its density (and thus on its chemical composition) and on its microstructure. The higher the density the lower is the water uptake and vice versa. Since the density of a layer correlates approximately with its refractive index n, a lower refractive layer will take up more water than a higher refractive layer. Accordingly a more compact layer with a large n will break over a lower refractive layer when the latter swells. This leads to the desired effect by a suitable selection of MeO layers.

If several metal layers are used, they can thus be selected such that after their conversion MeO/MeS microcracks occur in the uppermost layer but the lower layer(s), however, remain compact. This results in a hydrophilic segmented surface with additional improved hydrophilicity for the uptake of the sample liquid. In particular it would be conceivable to have a first layer made of silicon and provide a second topmost layer made of aluminum and to after-treat as described. The resulting Si—O layer can take up more water than the resulting Al—O layer so that this layer breaks over the Si—O layer.

The hydrophilicity of the surface of the embodiments of the spreading net described herein can also be increased by first of all setting up a defined micro-roughness or specifically introducing micro-particles during the production of the metallic layers. Thus, it would be possible to incorporate MeO particles (for example ZnO, TiO2 or ZrO2) into the plastic of the filaments and subsequently expose these particles.

Embodiments of the spreading nets can be integrated particularly simply into existing or new test systems. In particular gluing with conventional multilayer test strips is more reliable particularly in miniaturized systems than is the case for the previously used surfactant-coated spreading nets.

The spatial distribution of the hydrophilicity of a spreading net can be specifically controlled in order to optimize the transfer of the sample liquid from the surface of the spreading net to the detection layer of the test element. For example in the case of a fabric or net, metal is not coated or inadequately coated at its crossing points so that no hydrophilization takes place there due to the absence of conversion into MeO/MeS. Furthermore, the spreading net can be selectively covered in order to prevent metal coating and to specifically only hydrophilize selective areas of the spreading net for example the surface of the spreading net which later faces the detection layer of the test element. This reduces the uptake and retention of sample liquid in positions of the spreading net that are unimportant for the purposes of spreading and the transfer of sample liquid towards the detection layer is specifically improved and accelerated, and less sample liquid is lost.

As already mentioned in addition to hydrophilized areas it is also possible to produce hydrophobic areas of a spreading net by partial retention of the original hydrophobic spreading net surface (i.e. by selective Me-coating and conversion thereof into MeO.

However, it is also possible to subsequently coat an already continuous MeO-coated spreading net with substances which locally hydrophobize the spreading net or modify its MeO surface in other ways in a targeted and positionally accurate manner.

An advantageous measure is for example the already mentioned hydrophobization of the spreading net around the application site of a sample to be applied. In this case, an area generally around the hydrophilic application site is coated with a hydrophobizing agent (e.g. as a pure substance or from an aqueous or organic solution). Said agent can for example be an aliphatic wax in a suitable nonpolar solvent. However, it is also possible to use substances with for example hydrophilic-hydrophobic properties (e.g. in a chain-like molecule), the hydrophilic end of which or the end with an affinity for MeS/MeO then binds to the MeO layer and the hydrophobic end of which determines the new surface property of the spreading net. Longer chain (e.g. n=6 to n=20) hydrocarbons having a terminal group with an affinity for MeO e.g. aliphatic alcohols or thiols are for example also conceivable.

Thus, for example an MeO-coated spreading net can be partially hydrophobized without difficulty by coating it with a wax dissolved in xylol.

This is especially advantageous for miniaturized systems with small sample volumes.

An applied sample is selectively channeled through a defined cross-section of the spreading net by rolling off at the hydrophobic periphery of the sample application zone due to inner cohesion and is thus guided and spread onto the provided reaction area of a detection layer in a homogeneous, two-dimensionally uniform manner and at a reproducible rate.

As a result the signal generation becomes more reproducible and as a side effect the risk of sample-related contamination around the application area is minimized.

Furthermore, the geometry of the hydrophilized layer can be adapted to the geometry of the detection layer. The spatial distribution of the hydrophilicity can be generated by an appropriate spatial distribution of the metallic layer or by an appropriate spatial distribution of the after-treated area. The hydrophilic areas that are generated, can differ in their physical properties (absorption or reflection of light). The differences can be utilized for the production process and for quality assurance and can be optionally amplified by chemical or physical means for example by staining.

The hydrophilicity of the surface of a spreading net can be further modified by an additional coating with a wetting agent or hydrophilizing agent (usually an improvement or homogenization/equalization; in some cases it may also be an attenuation of the hydrophilicity). In this connection the local distribution of an additional or improved hydrophilicity can also be achieved by locally applying very small droplets of additional wetting agents.

The hydrophilizing agents are firstly wetting agents or dispersing additives in the broadest sense which are typically cationic, but in certain embodiments may actually be anionic or non-ionic, and which as a pure substance have previously mainly been present in a solid form at ambient temperatures but can now, however, also be used in a liquid form to avoid the disadvantages mentioned in the following. In certain uses, the liquid pure substance on an adsorbing MeO layer is provided, as for example in the description below on the irradiation of systems which contain spreading nets. Hydrophilizing agents which were not previously commonly used such as the non-ionic liquid surfactant polysorbate-20 can in particular also be used in conjunction with an MeO or MeS layer. In contrast to the known measures in the prior art, these surfactants can be used without undesired side-effects such as creeping or formation of zones of accumulation and depletion occurring. This is due to the fact that the already hydrophilic MeO or MeS surface layer has an adsorbing effect on the surfactant. Hence, the MeO or MeS surface layer can also be directly coated with a liquid non-ionic surfactant and the coating or wetting process proceeds more rapidly than is the case with conventional plastic spreading nets due to the adsorption process.

If it is necessary to sterilize such a system containing spreading nets by irradiation, the problem that a conventional wetting agent which is always an organic compound is destroyed by irradiation is also circumvented.

Furthermore, artifacts due to irradiation do not pass from the spreading net itself or only to a slight extent onto the hydrophilic spreading net surface because they are at least partially held back by the MeO layer.

Since such artifacts which are more likely to be hydrophobizing could impair the hydrophilic layer, the MeO layer in both cases consequently leads to an improved preservation of the surface hydrophilicity.

If the MeO layer is after-coated with a relatively small amount of a relatively irradiation-insensitive and liquid wetting agent, the hydrophilicity can be optimally preserved by the fact the quasi-liquid film in the MeO layer renews itself on the surface and as a result hydrophobic substances which penetrate from outside and also from the sides of the spreading net (filaments) are reduced or removed from the surface by dilution effects. In this case the term "from the sides of the spreading net" is intended to include that radiation can cause artifacts to escape from the plastic of the spreading net which have a hydrophobic effect. These are adsorbed by the MeS/MeO layer.

Due to the hydrophilicity and the adsorptive capacity of the MeO or MeS surface layer it is also possible to use other wetting agents which it has previously not been possible to use in the prior art for coating conventional spreading nets or could only be used with considerable effort or only for limited applications because they are not suitable for conventional plastic spreading nets with their hydrophobic surfaces. These are those hydrophilizing agents which do not have a wetting effect on these surfaces when applied from an aqueous solution and are therefore also not absorbed onto hydrophobic surfaces. Rather they do not have a (co)wetting effect until they come into contact with aqueous samples after they have already been applied to the surface. They for example include very polar hydrophilizing agents which are only soluble in water and which can now be applied directly from aqueous solutions onto the spreading nets treated according to the disclosed embodiments such as the salts of polyacids with a spreading effect. These hydrophilizing agents are ionic compounds which are applied to the first layer (first hydrophilic layer i.e. MeS/MeO layer) in a dissolved form for dilution during its formation or afterwards, and in this process are incorporated into the first layer or react with this layer and therefore permanently adhere to this layer.

Thus, it is possible to use more complex organic acids or salts or organic acids e.g. of polyacids which are either synthetic or of biological origin. These are for example polycarboxylic acids such as polyacrylic acids or polymethacrylates or salts (e.g. lithium or sodium salts) of sulfated polysaccharides such as e.g. of heparins or chondroitin sulfate or hyaluronic acid.

Furthermore, the ionic hydrophilizing agents can also be solutions of simple organic compounds or salts of organic compounds such as simple carboxylic acids, which for optional reasons of safety may be of natural origin. Thus, for example monocarboxylic or oligocarboxylic acids or also hydroxycarboxylic acids are mentioned e.g. succinic acid or gluconic acid or also lactic acid, malic acid, tartaric acid, citric acid or saccharic acid or salts thereof e.g. sodium, potassium or calcium salts thereof. Derivatives of phosphoric acids are also conceivable. In the case of salts, the coating may optionally take place in one step but it can also be in two steps by means of a first application of acid and then a neutralization with a base.

Thus, spreading nets with a hydrophilic MeO layer can now be coated with a wide variety of substances from an aqueous or at least partially aqueous-based solution which is very advantageous for the technical production implementation because no organic solvents have to be used.

Finally further molecules can be chemically attached to the functional oxygen-containing or sulfur-containing groups of the MeO or MeS layers, such as nucleic acids or proteins (enzymes, antibodies etc.) or synthetic wetting agents or biologically active molecules (such as anticoagulant substances or substances which trigger coagulation). It is also possible to attach substances which indicate a wetting with liquid for example by changing the light absorption or by fluorescence.

Since the surface of the embodiments of spreading nets, which surface has been modified with the MeO layer or MeS layer as described herein, can have adsorptive or reactive properties, it is possible to after-treat the surface with other substances in addition to the hydrophilizing agents and thus to change its properties. The MeO layer or MeS layer may for example have humidity-regulating properties because it adsorbs water or air humidity to a certain degree. This improves the humidity regulation especially in individually packaged test systems.

Even when using a fine spreading net it is thus overall possible to take up and pass on/transfer a larger sample volume per unit of area than was previously possible. As a result less sample liquid is lost and the detection of the respective measured variable is very successful even when using particularly fine spreading nets.

It is possible to generate local hydrophilic areas. When processing and subsequently manufacturing prefabricated sheet materials i.e. materials having a large surface area which are cut to size after treatment, the locally generated hydrophilic areas can be selectively cut out of the sheet material and specifically positioned on the chemical detection layer. In this process it is possible to also cut out a hydrophobic surrounding area so that the sample liquid only penetrates via the hydrophilic area of the spreading net and then spreads. As a result less sample liquid is wasted in the spreading net which means that it is possible to detect an analyte from a smaller initial amount of sample. Hence, the utilization of sample up to the start of the detection reaction is more efficient.

The hydrophilicity of the surface of the spreading net can also be utilized for further modifications of the surface with capillary conducting elements which results in further advantageous properties of the test elements according to the embodiments invention.

The hydrophilic surface can for example serve as a carrier material for binding materials which filter in an undirected or directed manner. These materials can also have a different structure than the spreading net itself. The spreading net with its at least partially hydrophilic surface can for example be used as a carrier for hydrophilic fibers which can even be fine or very fine. This results in a type of fleece and/or a contacting layer which at least partially leads away from the surface of the test element towards the sample to be applied. Plastic fibers as well as natural fibers for example fibers made of cellulose are suitable for this purpose. It is also possible to use very fine fibers with a thickness of less than about 50 μm and a length of about 10 to about 500 μm.

The hydrophilic fibers some of which project from the spreading net act as capillary conducting elements for the sample to be applied. They facilitate the passage of the sample from the sample collecting device onto the spreading net (so-called "through connection"). When the sample starts to cross over, the remaining sample is then also transferred and distributed by the spreading net to the detection layer of the test element according to the invention. In this connection the angle of the spreading net relative to the direction of transport of the sampling device can encompass all angles from about +0° to about 90°, up to about 180°. Embodiments having a 90° orientation have been found useful.

A symmetric or asymmetric hydrophilic membrane which also acts as a capillary-conducting element can also be applied to the at least partially hydrophilic surface of the spreading net. In this case the spreading net carries the membrane on its application side for the sample whereas the opposite side fulfils the transferring and spreading function in the direction of the detection layer.

The spreading net can also be embedded in a symmetric or asymmetric hydrophilic membrane where the membrane permeates and surrounds the spreading net i.e. the spreading net acts as a carrier within the membrane. For this purpose a membrane material is introduced into the interstices of the spreading net and is bound to the inventive hydrophilic areas of the surface of the spreading net. This arrangement also acts as a capillary conducting element as described above.

The spreading net can of course also be only provided partially or locally with a capillary conducting element and only have its effect in targeted selected areas of the spreading net in order to further optimize the transport of the sample from the sample collecting device to the detection layer of the test element.

The invention is to be explained in more detail by the following FIGURE and examples.

BRIEF DESCRIPTION OF THE DRAWINGS

The following detailed description of the embodiments of the present invention can be best understood when read in conjunction with the following drawing, where like structure is indicated with like reference numerals and in which:

FIG. 1 shows an analytical test element in a diagrammatic view.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

The test element 10 shown in FIG. 1 can be mounted on a single test strip or a large number of such test elements can be mounted spaced apart on a rollable test tape. The test element 10 has a carrier foil 12 which on one side is provided with a chemical detection layer 14. The detection layer 14 comprises a dry chemical system which reacts to a target substance or to an analyte by for example a color change when a sample is applied. The color change can be reflection-photometrically detected through the transparent carrier foil 12.

A spreading net 16 is arranged on the side of the detection layer 14 which faces away from the carrier foil 12 and facilitates a two-dimensional dispersion of sample on the detection layer 14. The sample is for example applied as a drop of blood on the free side of the spreading net 16. The spreading net 16 is generally formed by filaments 18 which have a mesh width of less than about 300 μm. In other embodiments, the mesh width is less than about 150 μm. In yet other embodiments, the mesh width is less than about 80 μm. Generally, the filaments 18 are interwoven in the form of a fabric mesh. The filaments 18 which for example comprise PET or PA are provided with a hydrophilic MeO/MeS surface layer 20 formed from a metal coating in order to facilitate sample dispersion on the detection layer 14 over a large area. The coating with metal can be carried out on the plastic filaments as a starting material or on the fabric meshes formed therefrom.

Suitable metals for the coating include all metals which can be applied by metal evaporation, sputtering or galvanic deposition because these coating methods are particularly simple to implement. It is also possible to deposit from a dissolved metal compound that has been applied to the filaments or finished structures (fabric, knitted fabrics, interlaced yarns).

The metallic layer (or the metallic filaments themselves) is subsequently oxidized by after-treatment for example with water, alkali hydroxides or alkaline earth hydroxides, oxygen (also atmospheric oxygen) under heat treatment. Then at least the surface of the metallic layer and where appropriate also the entire layer is converted into one or more metal oxides $Me_{(x)}O_{(y)}$, metal hydroxides $Me_{(x)}(OH)_{(2y)}$ or mixed forms thereof such as metal oxyhydroxides (metal oxyhydrates) $Me_{(x)}O_{(y-z)}(OH)_{(2z)} \cdot nH_2O$. For the sake of simplification all these layer types are referred to as "MeO layers" irrespective of their structure.

The MeO layers advantageously have a compact structure and are insoluble or poorly soluble in aqueous or aqueous/alcoholic systems. This structure is ensured by the chemistry of the metal compounds i.e. by a suitable selection of the metals or alloys.

Zn or Al are particularly suitable as a metal or alloy. Both readily react and especially Zn as a trace element is physiologically completely unproblematic. Plastic nets coated with aluminum or zinc or alloys containing these metals by metal evaporation or sputtering can be after-treated with hot water or steam, alkali hydroxides or alkaline earth hydroxides or simply by heat treatment under the action of oxygen so that at least the surface of the metal coating is oxidized.

For the medical field and in particular for medical diagnostics it is appropriate to use those metals which at least in small amounts are not toxic and well-tolerated, including certain components of the body (such as essential trace elements). Examples are magnesium, calcium, manganese, vanadium, silicon and zinc. The following are also tolerated well to very well: titanium, zirconium, silver, aluminum, tantalum, hafnium, niobium and mixtures or alloys thereof or mixtures or alloys with other elements. In this connection the spreading net provided according to the invention as part of the test element is at least a connecting member to the sample collecting element or lancing element even if a direct contact with the human body does not take place.

Small additions of other metals which are usual in the production process can be added to the mixtures as an accepted or even desired impurity such as for example hafnium or yttrium as additives to zirconium. Furthermore, a large amount of accompanying metals can be intentionally added as an alloy for example copper as an additive to aluminum in the form of the described insoluble hydrophilic compound.

The use of such compatible metals lends itself especially to analytical test elements such as for example those that are described in EP 1 039 298 B1, the disclosure of which is hereby incorporated herein by reference. The same applies to highly integrated test systems in particular in the field of medical diagnostics in which the test element is directly coupled to a sample collecting device for example a lancing element for blood collection. In one embodiments, zinc is used which is an example of a trace element where the daily requirement is for example increased in diabetics. It is also known that zinc can be dispensed to healthy individuals in the form of zinc acetate without a medical indication for example in the form of flavour enhancers in chewing gum. Therefore, it is possible to practically exclude any health concern due to a contamination with zinc especially since the recommended daily requirement is many orders of magnitude higher than a contamination. Aluminum is similarly unproblematic for medical fields of application even if it is also not an essential trace element.

In the case of highly integrated test systems it is additionally possible to coat the sample collection device (for example a lancet as a lancing element) with a surfactant as usual without impairing the hydrophilicity of the inventive MeO layer in the area of the test element. If the surfactant layer should migrate, non-ionic surfactants in particular can be adsorbed by the MeO layer without impairing its primary hydrophilicity. This prevents surfactant from reaching the detection layer of the test strip containing the dry chemicals and having a negative effect on its properties.

When fabrics are used, it is the finished fabric that is usually treated. It is, however, also possible to merely treat the warp or weft threads according to the invention before the weaving process. Furthermore, fabrics, knitted or woven fabrics which contain fine metal threads in variable percentages are also conceivable which have a stabilizing effect particularly in the case of very fine structures. In this case a partial treatment may also be sufficient.

In model experiments, foil material made of Mylar® (trade name for dimensionally-stable polyethylene terephthalate foils) was used. A thin aluminum layer was vapor deposited on the Mylar foils (referred to herein as: Mylar Alu). The aluminum layer was oxidized under the action of water vapor (e.g., see EP 1 037 717 B1; such an oxidized aluminum layer referred to herein as: Mylar-Alu-ox).

Example 1

Mylar-Alu-ox foil strips were pulled from the roll and cut off. The pieces were immersed for 1 minute in boiling demineralized water (in the following: VE water), then pulled out, pulled three times over the handle of tweezers in order to wipe off the water and hung to dry in the air.

Example 2

Mylar-Alu-ox foil strips were pulled from the roll and cut off. The pieces were immersed for 20 minutes at room temperature in 0.05% (w/w) lithium heparin in water (1 liter), then pulled out and washed twice for about 20 seconds with VE water, subsequently they were pulled three times over the handle of tweezers in order to wipe off the water and hung to dry in the air.

Example 3

Mylar-Alu foil material was cut out 1.5 cm wide from the area. The pieces were immersed for 20 minutes in boiling VE water, then pulled out and immediately immersed for 1 minute in 0.05% (w/w) lithium heparin in water (1 liter). Subsequently the pieces were pulled three times over the handle of tweezers in order to wipe off the water and hung to dry in the air.

Mylar-Alu-ox foil strips which were pulled from the roll and cut out but not after-treated served as a reference material for the following comparison. In order to compare each example with the reference material, the pieces were subjected to a known standardized material test for the Mylar-Alu-ox foil. In this material test the spreading effect on the material was determined ten times in each case in such a manner that the material was wetted with 8 µL test solution and its spread in mm (to an accuracy of 0.5 mm) was measured. The ten individual values were added and the mean thereof was calculated. The stated value is thus a parameter for the average linear spreading. An even more exact representation of the wetted area is obtained when the linear individual values are squared and only afterwards the average is calculated from the sum.

The results are summarized in the following table 1.

TABLE 1

| Spreading (mm) | Reference | Example 1 | Example 2 | Example 3 |
|---|---|---|---|---|
| 1 | 7.0 | 6.0 | 8.0 | 8.0 |
| 2 | 8.0 | 6.0 | 8.0 | 8.0 |
| 3 | 7.0 | 6.0 | 8.0 | 8.0 |
| 4 | 8.0 | 6.5 | 9.0 | 6.5 |
| 5 | 7.0 | 7.0 | 8.5 | 7.0 |
| 6 | 6.5 | 7.0 | 8.5 | 8.0 |
| 7 | 8.0 | 8.0 | 7.5 | 8.0 |
| 8 | 6.5 | 6.0 | 7.0 | 7.0 |
| 9 | 6.5 | 7.0 | 6.5 | 8.0 |
| 10 | 7.0 | 6.0 | 6.5 | 8.0 |
| mean | 7.2 | 6.6 | 7.8 | 7.7 |
| target | | ≥6.0 mm | | |

Comparison Reference/Example 1

The result shows that an impairment of the spreading effect is observed when the already hydrophilized Mylar-Alu-ox foil is immersed in hot water. Hence "refreshment" of the hydrophilization does not take place. Therefore, the experiments from examples 2 and 3 were carried out at room temperature.

Comparison Reference/Example 2

The additional coating with a wetting agent which was in this case lithium heparin results in a considerable improvement of the spreading effect.

Comparison Reference/Example 3

Oxidation of a Mylar-Alu foil material in hot water with subsequent treatment with a wetting agent (in this case lithium heparin) also results in a considerable improvement of the spreading effect.

In the following, experiments with a very finely meshed aluminum-coated spreading net are described, the aluminum layer of which is converted in experiments 1 to 4 into a boehmite layer (AlO(OH)) under varying conditions. After this hydrophilization by means of boehmite, tests were carried out with regard to wetting (penetration test and spreading) of the boehmite-coated spreading net with blood.

In order to carry out the penetration test, the spreading net was attached horizontally in a lying position over an opening. The area of the spreading net to be tested is thus open towards the top and bottom and only has contact with the air. A drop of blood applied to the spreading net will remain on its "surface" and not penetrate into the spreading net fabric in the case of a hydrophobic spreading net especially when it has a very fine mesh. However, if the spreading net is hydrophilic, the sample will penetrate and will at least partially emerge from the lower "surface" or side and be visible i.e. the drop of blood "is suspended". This indicates that the hydrophilization has succeeded.

For the spreading test the spreading net lies horizontally and unfastened and as flat as possible over a detection layer. However, for experimental reasons the spreading net is not always completely flat due to the non-optimized production process. This also applies to the unprocessed detection layer. However, planarity is essential for the spreading behavior (capillary forces). This also results in variations in the spreading behavior which only become negligible in optimized and secured analytical test elements.

The results are summarized in the following table 2.

TABLE 2

| Material[1] (spreading net) | Experiment No. | Penetration test | Spreading/remark | Spreading [mm × mm] |
|---|---|---|---|---|
| 07-51/33 + boehmite | 1 | hardly penetrates | spreads well, a small amount of residual blood is still present at the end | 8 × 12 |
| 07-51/33 + boehmite | 2 | penetrates well | spreads very well, a small amount of residual blood is still present at the end | 8 × 12 |
| 07-51/33 + boehmite | 3 | does not penetrate | spreads best | 10 × 15 |
| 07-51/33 + boehmite | 4 | penetrates well | spreads well, it was β-irradiated followed by storage | 8 × 12 |

[1]The commercially available spreading net SEFAR PETEX 07-51/33 used for the experiments listed in table 2 consists of monofilament plastic threads of a polyester, in this case PET (polyethylene terephthalate). The mesh width is w = 51 μm and the open sieve area is a0 = 33%, i.e. 67% of the total area consists of the perpendicular projection of PET threads. The yarn diameter is d = 38 μm and the height of the spreading net h = 60 μm.

Heparinized venous blood with a hematocrit value of 41% was used.

The results of the conversion of the aluminum layer and on the wetting behavior of the spreading net are discussed in the following.

The conversion into boehmite succeeded with the spreading net that was used in 4 experiments with apparatus-related limitations (see below) and variations in the experimental conditions which are easily controllable in an established process after its optimization.

Using the very fine spreading net 07-51/33 it was shown that a boehmite layer on a PET spreading net is so hydrophilic that it results in a spreading of blood.

In this case the aluminum layer thickness on the starting material and the experimental set-up and procedure ("handling") were not optimized. For experimental reasons it is not possible to keep the temperature and thus the turbulence of the boiling water used for conversion completely constant. The pieces of spreading net swirl in the water-bath, fold up and have to be continuously agitated. Hence, it is not possible to ensure that the boiling water acts uniformly over the area and with respect to time. The removal and drying is also not very reproducible and the hot net is very prone to creasing.

The spreading net used in experiments 1 to 4 in table 2 was subjected to further experiments after conversion of the aluminum layer into the boehmite layer with the aim of carrying out a secondary coating with a conventional wetting agent or other substances with a spreading effect ("wetting agent variations"). Subsequently tests were also carried out in this case with respect to wetting (penetration test and spreading) of the spreading net with blood. The results are summarized in table 3. For this purpose various strips (strips) (A) to (M) of the spreading net provided with a boehmite layer from experiment 2 of table 2 were used to which various wetting agents listed in table 3 were added. All experiments were carried out in an aqueous solution.

The letters A to K denote different wetting agents at different concentrations. For production related reasons those remaining strips cut from letter M onwards only had boehmite but no additional wetting agent. M is thus the reference because M spreads very well as seen in table 2. It was expected that changes due to additional wetting agents (on boehmite) can be better discriminated on this material.

TABLE 3

| Experiment No. | Material spreading net (SN) (strip) + boehmite + wetting agent | Penetration test | Spreading/remarks[2] | Spreading [mm × mm] |
|---|---|---|---|---|
| 1 | SN (M) only boehmite | penetrates very well | spreads very well | 8 × 12 |
| 2 | SN (A) + boehmite + 0.1% DONS | penetrates very well | spreads well | 18 × 18 |
| 3 | SN (B) + boehmite + 0.2% DONS | penetrates very well | spreads almost as well as No. 1 | 20 × 20 |
| 4 | SN (C) + boehmite + 0.5% DONS | penetrates very well | spreads somewhat less than No. 1 | 17 × 17 |
| 5 | SN (D) + boehmite + 0.3% Geropon T77 | penetrates | spreads asymmetrically in parts | 12 × 12 |
| 6 | SN (E) + boehmite + 0.325% Rhodapex CO 436 | penetrates | spreads slower than No. 1 | 15 × 15 |
| 7 | SN (F) + boehmite + li-heparin 0.05% | penetrates | spreads moderately relative to No. 1 (does not lie well) | n.s. |
| 8 | SN (G) + boehmite + li-heparin 0.01% | penetrates | spreads moderately (does not lie flat) | n.s. |
| 9 | SN (H) + boehmite + 75 i.U. heparin | penetrates | does not lie completely flat | — |
| 10 | SN (I) + boehmite + 0.01% PAA | penetrates | spreads moderately and asymmetrically (nonplanar) | — |
| 11 | SN (J) + boehmite + Na heparin 0.01% | does not penetrate | does not lie planar | — |
| 12 | SN (K) + boehmite + PS 20 0.2% | does not penetrate | spreads relatively fast (~as No. 1 and symmetrically) | 15 × 15 |

[2]No. 1 in relation to conventional, coarser spreading net; experiments No. 2-12 relative to No. 1.
n.s. = not specified because not flat Heparinized venous blood with a hematocrit value of 41% was used.

Results on the wetting behavior of the secondary coating:

The very fine spreading net 07-51/33 gives good results with regard to the penetration of a blood drop on a "freely suspended" spreading net as well as with regard to the spreading on a secondary coating. In this case neither the aluminum layer itself nor its conversion into boehmite nor the secondary coating (wetting agent) were optimized.

In particular this very fine spreading net shows the feasibility of the hydrophilization by means of a (or via a) boehmite layer using only aqueous coating systems.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A process for producing a test element comprising the steps of:
   providing a surface comprising a chemical detection layer;
   preparing a spreading net by:
      coating a filament structure with a metallic layer, wherein the filament structure of the spreading net comprises one of metallic filaments and plastic filaments; and
      oxidizing at least a surface portion of the metallic layer coated on the filament structure, wherein the oxidizing step comprises exposing at least the surface of the metallic layer to an oxygen-containing or sulfur-containing oxidant, and wherein the spreading net is configured for providing a planar distribution of a liquid sample on the chemical detection layer; and
   disposing the spreading net on the chemical detection layer of the surface.

2. The process according to claim 1, wherein the oxidizing step comprises exposing at least a surface of the metallic layer to water, oxygen, alkali hydroxide or alkaline earth hydroxide.

3. The process according to claim 1, wherein the oxidizing step further comprises after-treating the metallic layer with a sulfur-containing compound.

4. The process according to claim 1, further comprising the step of after-treating the spreading net with at least one additional hydrophilizing agent.

5. The process according to claim 4, wherein the at least one additional hydrophilizing agent comprises an anionic or non-ionic surfactant.

6. The process according to claim 5, wherein the agent comprises a non-ionic surfactant comprising a liquid comprising a substantially pure substance in the temperature range of the desired use of the test element produced by the process.

7. The process according to claim 4, wherein the at least one hydrophilizing agent is an at least substantially water-soluble compound comprising one of an organic acid or a salt thereof, or an organic polyacid or a salt thereof.

8. The process according to claim 1, wherein the oxidizing step further comprises after-treating the metallic layer with a radiation-insensitive liquid wetting agent.

9. The process according to claim 1, further comprising the step of providing the oxidized metallic layer with one or more of hydrophilic surface areas and hydrophobic surface areas.

10. The process according to claim 9, wherein providing the oxidized metallic layer with the one or more hydrophilic surface areas and hydrophobic surface areas comprises one or both of selectively coating only portions of the filament structure with the metallic layer prior to the oxidizing step, and selectively oxidizing only portions of the surface of the metallic layer coated on the filament structure.

11. The process according to claim 9, wherein providing the oxidized metallic layer with the one or more hydrophilic surface areas and hydrophobic surface areas comprises coating defined areas of the oxidized metallic layer with a hydrophobizing agent.

12. The process according to claim 1, wherein the step of oxidizing at least a surface portion of the metallic layer is configured to be performed such that at least a portion of metallic material of the metallic layer is retained wherein the metallic material maintains conductivity and ability to undergo electrostatic charging and discharging.

13. The process according to claim 12, further comprising the step of electrostatically controlling at least one targeted portion of the spreading net.

14. The process according to claim 9, wherein the step of providing the oxidized metallic layer with one or more hydrophilic surface areas and hydrophobic surface areas comprises providing one or more hydrophilic surface areas each configured as a carrier for hydrophilic fibers.

15. The process according to claim 14, further comprising the step of providing the one or more hydrophilic surface areas with hydrophilic fibers a plurality of which are configured to project from the spreading net so to act as capillary conducting elements for a sample to be applied to the test element.

* * * * *